US010185850B2

(12) United States Patent
Benedetti et al.

(10) Patent No.: US 10,185,850 B2
(45) Date of Patent: Jan. 22, 2019

(54) METHOD FOR STORING TEMPORARY DATA IN A MEMORY OF AN RFID TAG ASSOCIATED WITH A CONSUMABLE OF A LABORATORY INSTRUMENT AND SYSTEM COMPRISING A LABORATORY INSTRUMENT, CONSUMABLE AND RFID TAG

(71) Applicant: Roche Diagnostics Operations, Inc., Indianapolis, IN (US)

(72) Inventors: Riccardo Leone Benedetti, Fehraltorf (CH); Gregor Hotz, Zug (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 44 days.

(21) Appl. No.: 15/380,136

(22) Filed: Dec. 15, 2016

(65) Prior Publication Data

US 2017/0177913 A1    Jun. 22, 2017

(30) Foreign Application Priority Data

Dec. 18, 2015   (EP) ..................................... 15201314

(51) Int. Cl.
*H04Q 5/22*     (2006.01)
*G06K 7/10*     (2006.01)
(Continued)

(52) U.S. Cl.
CPC ....... *G06K 7/10366* (2013.01); *G06F 19/366* (2013.01); *G06K 19/07309* (2013.01); *G16H 10/40* (2018.01)

(58) Field of Classification Search
CPC ..................... G06K 7/10366; G06K 19/07309
(Continued)

(56) References Cited

U.S. PATENT DOCUMENTS

2005/0159982 A1    7/2005  Showalter et al.
2011/0022331 A1*   1/2011  Clinton .................... B01L 3/54
                                                    702/27
(Continued)

FOREIGN PATENT DOCUMENTS

EP          2367010 A2      9/2011
JP       2004-271299 A      9/2004
(Continued)

*Primary Examiner* — Dhaval V Patel
(74) *Attorney, Agent, or Firm* — Roche Diagnostics Operations, Inc.

(57) ABSTRACT

A method for storing temporary data in a memory of a RFID tag associated with a consumable of a laboratory instrument for processing a reagent or biological sample is disclosed. The method comprises providing the RFID tag associated with the consumable. The RFID tag comprises a memory. The memory comprises a user memory configured to store user data and a system memory configured to store system data. The laboratory instrument writes the temporary data into the system memory. The temporary data are associated with a process to be carried out by the laboratory instrument. Further, a system comprising a laboratory instrument for processing a reagent or biological sample, a consumable and a RFID tag associated with the consumable is disclosed. The laboratory instrument is configured to carry out the method.

20 Claims, 2 Drawing Sheets

(51) Int. Cl.
*G16H 10/40* (2018.01)
*G06K 19/073* (2006.01)
*G06F 19/00* (2018.01)

(58) Field of Classification Search
USPC .......... 340/10.51, 10.1, 10.42, 10.52, 572.1, 340/572.8, 5.8
See application file for complete search history.

(56) References Cited

U.S. PATENT DOCUMENTS

2015/0104796 A1  4/2015  Goemann-Thoss et al.
2015/0145652 A1* 5/2015  Weidinger ........... G06K 7/0008
                                                    340/10.51

FOREIGN PATENT DOCUMENTS

JP   2012-189379 A   10/2012
WO   2008/024471 A2   2/2008

\* cited by examiner

METHOD FOR STORING TEMPORARY DATA IN A MEMORY OF AN RFID TAG ASSOCIATED WITH A CONSUMABLE OF A LABORATORY INSTRUMENT AND SYSTEM COMPRISING A LABORATORY INSTRUMENT, CONSUMABLE AND RFID TAG

CROSS-REFERENCE TO RELATED APPLICATIONS

This application claims priority to EP 15201314.0, filed Dec. 18, 2015, which is hereby incorporated by reference.

BACKGROUND

The present disclosure generally relates to a method for storing temporary data in a memory of an RFID tag associated with a consumable of a laboratory instrument and system comprising a laboratory instrument, consumable and an RFID tag.

Laboratory instruments in the field of the disclosed method/system process reagents or biological sample. With such laboratory instruments, RFID tags are provided on reagent containers for automatic analyzers. The RFID tag comprises a memory divided into two parts. The first part is the so called user memory and the second part is the so called system memory or configuration area. Within the user memory, the user data are stored. Direct read or write access to this part of the memory is possible depending on the related write protection conditions. Within the system memory, all required information is stored, such as the unique identifier (UID), write protection, access control information, passwords, application family identifier (AFI) and electronic article surveillance (EAS). This memory area cannot be directly accessed.

It is known to store temporary dynamic process/workflow data in a database. If needed, the UID is read from the RFID tag and compared to stored data in the database or used as pointer/identifier/reference number to look up. The user memory part on the RFID tag is used for more permanent data like reagent information, expiration date, analyzer used and the like.

It is also known to use RFID tags on in vitro diagnostics containers. The UID or any functional equivalent identifier is assigned and programmed by the RFID integrated circuit manufacturer. Thus, the UID or any functional equivalent identifier cannot be altered and guarantees the uniqueness of each label. Regarding the UID or any functional equivalent identifier, password protected EAS and AFI functionality, the EAS/AFI password enables the addressed label to be set in a mode where the EAS status and the AFI value can only be changed if the correct EAS/AFI password is transmitted to the label within the mentioned commands. It is to be noted that password protection is optional. Some RFID integrated circuits have AFI and data storage format identifier (DSFID) without password protection. Temporarily dynamic process/workflow data is usually stored in the user memory part on the RFID tag. For example, the information on which analyzer a reagent is used is written to the user memory part.

However, the communication and checking/looking-up with the database slows down the workflow. Depending on the amount and velocity of involved mechanics of, for example, reagent storage or sample transport, the communication with a database could thwart the process, especially extending to large pre- or post-analytic storage or transport units. In addition to mechanical factors also electrical factors could thwart the process such as access time to data base and real time network availability.

If the user memory part of the RFID tag is used, the whole data concept of information on a tag will be affected and memory capacity for more permanent information like reagent fluid content or expiration date will be reduced. In addition, during production of reagents and reagent container with the tag, the exact storage area needs to be defined and has to be kept free for dynamic/temporary data. This will lead to a huge effort in agreement between different departments or companies that are stakeholders of the RFID data concept. Another drawback of using the user memory part for storing of temporary data is that this memory part is grouped in bigger sections, i.e. the so called blocks and/or sections. The memory area that needs to be read or written will be one or multiple block(s) depending on the data size and allocation. Another important drawback is caused due to the fact that the UID is stored in the system memory of the tag and any temporary data will be stored in the user memory part. Thus, it would need at least two reading commands to link the UID to these temporary data, which again slows down the workflow. In some cases, even more commands are necessary to access the special section/block on the tag to read the corresponding temporary data.

SUMMARY

According to the present disclosure, a system and method for storing temporary data in a memory of a RFID tag associated with a consumable of a laboratory instrument for processing a reagent or biological sample are presented. The method can comprise providing the RFID tag associated with the consumable. The RFID tag can comprise a memory. The memory can comprise a user memory configured to store user data and a system memory configured to store system data. The method can also comprise writing the temporary data by the laboratory instrument into the system memory. The temporary data can be associated with a process to be carried out by the laboratory instrument.

Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
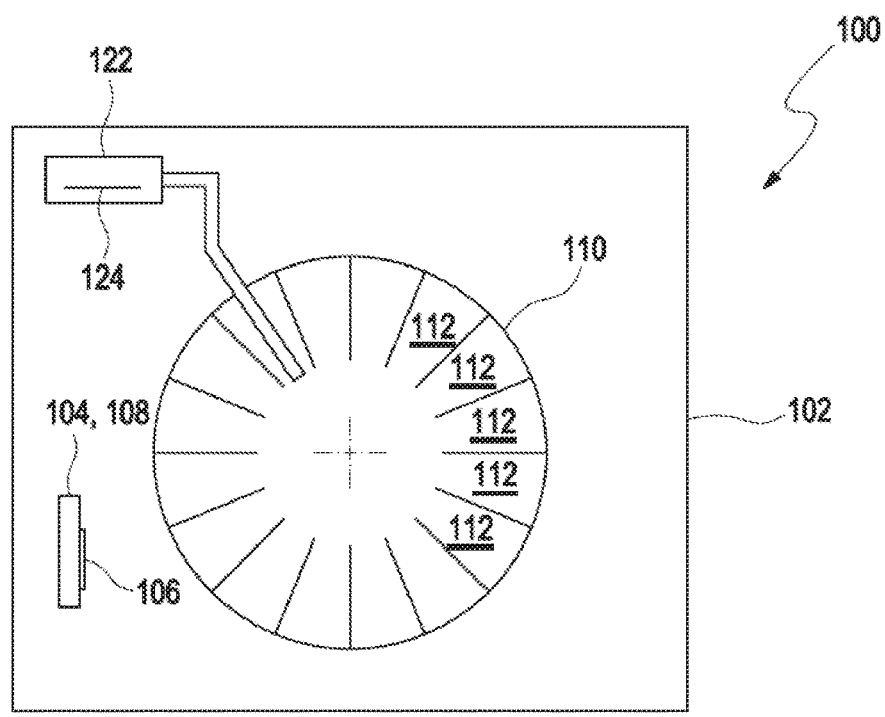
FIG. 1 illustrates a perspective view of a system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

As used in the following, the terms "have," "comprise" or "include" or any arbitrary grammatical variations thereof can be used in a non-exclusive way. Thus, these terms may both refer to a situation in which, besides the feature introduced by these terms, no further features can be present in the entity described in this context and to a situation in which one or more further features can be present. As an example, the expressions "A has B," "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically can be used only once when introducing the respective feature or element. In the following, in most cases, when referring to the respective feature or element, the expressions "at least one" or "one or more" cannot be repeated, non-withstanding the fact that the respective feature or element may be present once or more than once.

Further, as used in the following, the terms "particularly," "more particularly," "specifically," "more specifically" or similar terms are used in conjunction with features of particular or alternative embodiment(s), without restricting alternative possibilities. The disclosed method/system may, as the skilled person can recognize, be performed by using alternative features. Similarly, features introduced by "in an embodiment of the disclosed method/system" or similar expressions are intended to be additional and/or alternative features, without any restriction regarding alternative embodiments, without any restrictions regarding the scope of the disclosed method/system and without any restriction regarding the possibility of combining the features introduced in such way with other optional or non-optional features of the disclosed method/system.

According to the disclosed method/system, a method for storing temporary data in a memory of a RFID tag associated with a consumable of a laboratory instrument for processing a reagent or biological sample is disclosed. The method can comprise providing the RFID tag associated with the consumable. The RFID tag can comprise a memory. The memory can comprise a user memory configured to store user data and a system memory configured to store system data. The laboratory instrument can write the temporary data into the system memory. The temporary data can be associated with a process to be carried out by the laboratory instrument.

The term "system memory" can be synonymously used with the term "configuration area."

The term "temporary data" as used herein can refer to dynamic data stored in or written into the system memory and which may be also cleared therefrom during a process of the laboratory instrument.

The term "laboratory instrument" as used herein can encompass any apparatus, or apparatus component, operable to execute one or more processing steps/workflow steps on one or more biological samples and/or reagents. The term "processing step" thereby can refer to physically executed processing steps such as centrifugation, aliquotation, sample analysis and the like. The term "instrument" can cover pre-analytical sample work-cells, post-analytical sample work-cells as well as analytical work-cells.

The term "reagents" as used herein can refer to reagents necessary for performing the analysis of analytes and can include reagents for sample preparation, control reagents, reagents for reacting with the analyte to obtain a detectable signal, and/or reagents necessary for detecting the analyte. Such reagents may include reagents for isolating an analyte and/or reagents for processing a sample and/or reagents for reacting with an analyte to obtain a detectable signal and/or washing reagents and/or diluents. Such reagents may be provided in a reagent vessel or reagent cassette. A reagent cassette can refer to a container comprising a liquid or suspension of reagents. Alternatively, a reagent cassette can be a holder for holding containers comprising a liquid or a suspension of reagents.

As the temporary data associated with a process to be carried out by the laboratory instrument are written into the system memory, only one operation and command, respectively, may be needed to identify and read the data as compared to two operations and commands, respectively, needed if data are stored in the user memory. By using only a single command, such as "Get System Information" as defined in ISO/IEC 15693-3, the UID as well as the stored temporary data can be transmitted from the RFID tag to a RFID reader resulting in a very fast identification of the UID plus the dynamic or temporary data. Thus, a lot of communication time may be saved and the process carried out by the laboratory instrument can be accelerated if compared to a process in which data have to be read from the user memory.

The system memory may comprise special function bytes. The special function bytes can be used to store the temporary data.

The term "special function bytes" as used herein can refer to the bytes of the system memory such as application family identifier (AFI) or data storage format identifier (DSFID). A memory can be organized in a specific manner. For example, a RFID Chip Memory organization may be based on the ISO standards ISO/IEC 15693. The respective 1024 bit electrically erasable programmable read only memory (EEPROM) can be divided into 32 blocks. A block can be the smallest access unit. Each block can comprise of 4 bytes (1 block=32 bits). Bit 0 in each byte can represent the least significant bit (LSB) and bit 7 the most significant bit (MSB), respectively. Thereby, the UID, as well as the value of these special function bytes, can be transmitted from the RFID tag to the RFID reader resulting in a very fast identification of UID plus dynamic data. Needless to say, there can be integrated circuits with different memory sizes out in the market. There can also be integrated circuits with different memory blocks out in the market. Further, there can be integrated circuits with different memory blocks widths out in the market, e.g., 32 bit or 64 bit block width.

The consumable may be at least one element selected from the group comprising of: reagent vessel, biological sample vessel, pipetting tip, and cuvette. Thus, the method may be applied to every consumable used with a laboratory instrument.

The process may comprise process steps. The temporary data can be associated with the process steps. The temporary data can be written into the system memory each time the consumable enters one of the process steps and can be cleared when the consumable terminates one of the process steps. Thus, the data may be written into and cleared from the system memory in a fast, or dynamic, manner such that the process can be accelerated. Further, no communication with an external data system may be necessary.

The temporary data may comprise information on the consumable. Thus, the laboratory instrument may be informed on the consumable and manage the process to be carried out.

The laboratory instrument may comprise a control unit. The control unit can write the temporary data into the system memory. As a laboratory instrument can usually comprise a control unit, this control unit may be adapted to write the temporary data into the system memory. Thus, no further device may be necessary for the writing process but the components present within the laboratory instrument may be adapted or modified to fulfill the writing function.

The control unit may read the temporary data written into the system memory. As a laboratory instrument can usually comprise a control unit. This control unit may be adapted to read the temporary data from the system memory. Thus, no further device may be necessary for the reading process but the components present within the laboratory instrument may be adapted or modified to fulfill the reading function.

The temporary data written into the system memory may be transmitted to the control unit by a command issued from the control unit. Particularly, only one single command may be needed to identify the RFID tag and read the temporary data as compared to two commands needed if data are stored in the user memory. By using only a single command, such as "Get System Information" as defined in ISO/IEC 15693-3, the UID as well as the stored temporary data can be transmitted from the RFID tag to a RFID reader of the control unit resulting in a very fast identification of the UID plus the dynamic or temporary data. It can be noted that a RFID reader can be capable to read and write data. Thus, a lot of communication time may be saved and the process carried out by the laboratory instrument can be accelerated if compared to a process in which data have to be read from the user memory.

The information may include at least one element selected from the group comprising: target position of the consumable, actual position of the consumable, state of the consumable, type of the consumable and content of the consumable. Thus, a lot of information may be stored in the system memory. The actual position of item can be determined by other means and can be initially stored into these special bytes. In case of a power down, or manually reloading, the target position in the memory can match the one retrieved with other means, e.g., encoder of the instrument.

The consumable may be a vessel configured to store a reagent or biological sample. For example, the vessel may be a sample tube, reagent cassette or a reagent container. The laboratory instrument may comprise a rotor comprising a plurality of compartments configured to receive the vessel. In other words, each of the plurality of compartments can be configured to receive a vessel. Thus, the rotor can basically provide a plurality of potential positions for a vessel. The temporary data may comprise information on a target and/or actual position of the vessel on the rotor. The target position can be associated with one of the compartments. Thus, the position where the vessel is to be disposed and/or the current position of the vessel may be stored as information within the system memory. Accordingly, a dynamic tracking of the vessel can be possible.

The control unit may check whether an actual position of the vessel on the rotor corresponds to the target position. Thus, the control unit can check whether the vessel is disposed at its correct position on the rotor.

The control unit may check whether the actual position of the vessel on the rotor corresponds to the target position based on a quality of a signal transmitted from RFID tag of the vessel to the control unit. As the signal quality and strength, respectively, can decrease with increasing distance of the RFID tag to the RDID reader, a deviation of the actual position from the target position may be detected if the actual signal does not correspond to the target signal. Thus, by a simple comparison of the actual signal with a target signal, it may be detected whether the actual positon corresponds to the target positon or not.

A plurality of consumables may be provided. The control unit can identify and/or locate one of the consumables by issuing a command and receiving a response signal from the one consumable. Locating can work in conjunction by matching with other sensors or by checking the sequence of consecutive position reads. Thus, the command can ensure that only a response signal is received from that consumable with which the control unit wants to communicate. Accordingly, the control unit can be prevented from receiving any information from other consumables than a target consumable.

Further, according to the disclosed method/system, a system comprising a laboratory instrument for processing a reagent or biological sample, a consumable and a RFID tag associated with the consumable is disclosed. The RFID tag can comprise a memory. The memory can comprise a user memory configured to store user data and a system memory configured to store system data of the integrated circuit. The laboratory instrument can be configured to carry out the above method of the disclosed method/system. As the temporary data associated with a process to be carried out by the laboratory instrument are writable into the system memory, only one operation and command, respectively, may be needed to identify and read the data as compared to two operations and commands, respectively, needed if data are stored in the user memory. By using only a single command, such as "Get System Information" as defined in ISO/IEC 15693-3, the UID as well as the stored temporary data can be transmitted from the RFID tag to a RFID reader resulting in a very fast identification of the UID plus the dynamic or temporary data. Thus, a lot of communication time may be saved and the process carried out by the laboratory instrument can be accelerated if compared to a process in which data have to be read from the user memory. Temporary data may be written in the system memory.

The system memory may comprise special function bytes. The special function bytes can be configured to temporary store the temporary data. Thereby, the UID as well as the value of these special function bytes can be transmitted from the RFID tag to the RFID reader resulting in a very fast identification of UID plus dynamic data.

The consumable may be at least one element selected from the group comprising of: reagent vessel, biological sample vessel, pipetting tip, and cuvette. Thus, the system may use every consumable used with a laboratory instrument.

The temporary data may be associated with a process to be carried out by the laboratory instrument. Particularly, the process may comprise process steps. The temporary data can be associated with the process steps. The laboratory instrument can be configured to write the temporary data into the system memory each time the consumable enters one of the process steps and can be cleared when the consumable terminates one of the process steps. Thus, the data may be written into and cleared from the system memory in a fast or dynamic manner such that the process can be accelerated. Further, no communication with an external data system may be necessary.

The temporary data may comprise information on the consumable. Thus, the laboratory instrument may be informed on the consumable and manage the process to be carried out.

The laboratory instrument may comprise a control unit. The control unit can be configured to write the temporary data into the system memory. As a laboratory instrument can usually comprise a control unit. This control unit may be adapted to write the temporary data into the system memory. Thus, no further device may be necessary for the writing process but the components present within the laboratory instrument may be adapted or modified to fulfill the writing function.

The control unit may be configured to read the temporary data written into the system memory. As a laboratory instrument can usually comprise a control unit. This control unit may be adapted to read the temporary data from the system memory. Thus, no further device may be necessary for the reading process but the components present within the laboratory instrument may be adapted or modified to fulfill the reading function.

The control unit may be configured to issue a command for transmitting the temporary data written into the system memory. Particularly, only one single command may be needed to identify the RFID tag and read the temporary data as compared to two commands needed if data are stored in the user memory. By using only a single command, such as "Get System Information" as defined in ISO/IEC 15693-3, the UID as well as the stored temporary data can be transmitted from the RFID tag to a RFID reader of the control unit resulting in a very fast identification of the UID plus the dynamic or temporary data. Thus, a lot of communication time may be saved and the process carried out by the laboratory instrument can be accelerated if compared to a process in which data have to be read from the user memory.

The control unit may comprise an antenna configured to read the temporary data. Thus, a simple receiver for receiving the transmitted signal can be provided.

The information may include at least one element selected from the group comprising: target position of the consumable, actual position of the consumable, state of the consumable, type of the consumable and content of the consumable. Thus, a lot of information may be stored in the system memory.

The consumable may be a vessel configured to store a reagent or biological sample. For example, the vessel may be a sample tube, reagent cassette or a reagent container. The laboratory instrument may comprise a rotor comprising a plurality of compartments configured to receive the vessel. In other words, each of the plurality of compartments can be configured to receive a vessel. Thus, the rotor can basically provide a plurality of potential positions for a vessel. The temporary data may comprise information on a target and/or actual position of the vessel on the rotor. The target position can be associated with one of the compartments. Thus, the position where the vessel is to be disposed and/or the current position of the vessel may be stored as information within the system memory. Accordingly, a dynamic tracking of the vessel can be possible.

The control unit may be configured to check whether an actual position of the vessel on the rotor corresponds to the target position. Thus, the control unit checks whether the vessel can be disposed at its correct position on the rotor.

The control unit may be configured to check whether the actual position of the vessel on the rotor corresponds to the target position based on a quality of a signal transmitted from the RFID tag of the vessel to the control unit. As the signal quality and strength, respectively, decreases with increasing distance of the RFID tag to the RDID reader, a deviation of the actual position from the target position may be detected if the actual signal does not correspond to the target signal. Thus, by a simple comparison of the actual signal with a target signal, it may be detected whether the actual positon corresponds to the target positon or not.

The system may further comprise a plurality of consumables. The control unit can be configured to identify one of the consumables by issuing a command and receiving a response signal from the one consumable. Thus, the command can ensure that only a response signal can be received from that consumable with which the control unit wants to communicate. Accordingly, the control unit can be prevented from receiving any information from other consumables than a target consumable.

The disclosed method/system can further disclose and propose a computer program including computer-executable instructions for performing the method according to the disclosed method/system in one or more of the embodiments enclosed herein when the program can be executed on a computer, or computer network. Specifically, the computer program may be stored on a computer-readable data carrier. Thus, specifically, one, more than one or even all of the method steps as indicated above may be performed by using a computer, or a computer network, preferably by using a computer program.

The disclosed method/system can further disclose and propose a computer program product having program code, in order to perform the method according to the disclosed method/system in one or more of the embodiments enclosed herein when the program can be executed on a computer or computer network. Specifically, the program code may be stored on a computer-readable data carrier.

Further, the present disclosure can disclose and propose a data carrier having a data structure stored thereon, which, after loading into a computer, or computer network, such as into a working memory, or main memory, of the computer, or computer network, may execute the method according to one or more of the embodiments disclosed herein.

The present disclosure can further propose and disclose a computer program product with program code stored on a machine-readable carrier, in order to perform the method according to one or more of the embodiments disclosed herein, when the program is executed on a computer, or computer network. As used herein, a computer program product can refer to the program as a tradable product. The product may generally exist in an arbitrary format, such as in a paper format, or on a computer-readable data carrier. Specifically, the computer program product may be distributed over a data network.

Finally, the present disclosure can propose and disclose a modulated data signal which can contain instructions readable by a computer system, or computer network, for performing the method according to one or more of the embodiments disclosed herein.

Referring to the computer-implemented aspects of the present disclosure, one or more of the method steps or even all of the method steps of the method according to one or more of the embodiments disclosed herein may be performed by using a computer, or computer network. Thus, generally, any of the method steps including provision and/or manipulation of data may be performed by using a computer, or computer network. Generally, these method steps may include any of the method steps, typically except for method steps requiring manual work, such as providing the samples and/or certain aspects of performing the actual measurements.

Specifically, the disclosed method/system can further disclose:

a computer or computer network comprising at least one processor, wherein the processor can be adapted to perform the method according to one of the embodiments described in this description, a computer loadable data structure that can be adapted to perform the method according to one of the embodiments described in this description while the data structure can be executed on a computer, a computer program, wherein the computer program can be adapted to perform the method according to one of the embodiments described in this description while the program can be executed on a computer, a computer program comprising a program for performing the method according to one of the embodiments described in this description while the computer program can be executed on a computer or on a computer network, a computer program comprising a program according to the preceding embodiment, wherein the program can be stored on a storage medium readable to a computer, a storage medium, wherein a data structure can be stored on the storage medium and wherein the data structure can be adapted to perform the method according to one of the embodiments described in this description after having been loaded into a main and/or working storage of a computer or of a computer network, and a computer program product having a program code, wherein the program code can be stored or are stored on a storage medium, for performing the method according to one of the embodiments described in this description, if the program code can be executed on a computer or on a computer network.

Summarizing the findings of the disclosed method/system, the following embodiments are disclosed:

A method for storing temporary data in a memory of an RFID tag associated with a consumable of a laboratory instrument for processing a reagent or biological sample is presented. The method can comprise providing the RFID tag associated with the consumable. The RFID tag can comprise a memory. The memory can comprise a user memory configured to store user data and a system memory configured to store system data of the integrated circuit. The laboratory instrument can write the temporary data into the system memory. The temporary data can be associated with a process to be carried out by the laboratory instrument.

The system memory can comprise special function bytes. The special function bytes can be used to store the temporary data.

The consumable can be at least one element selected from the group comprising of: reagent vessel, biological sample vessel, pipetting tip, and cuvette.

The process can comprise process steps. The temporary data can be associated with the process steps. The temporary data can be written into the system memory each time the consumable enters one of the process steps and can be cleared when the consumable terminates one of the process steps. The temporary data can comprise information on the consumable.

The laboratory instrument can comprise a control unit. The control unit can write the temporary data into the system memory. The control unit can read the temporary data written into the system memory. The temporary data written into the system memory can be transmitted to the control unit by a command issued from the control unit.

The information can include at least one element selected from the group comprising: target position of the consumable, actual position of the consumable, state of the consumable, type of the consumable and content of the consumable.

The consumable can be a vessel configured to store a reagent or biological sample. The laboratory instrument can comprise a rotor comprising a plurality of compartments configured to receive the vessel. The temporary data can comprise information on a target and/or actual position of the vessel on the rotor. The target position can be associated with one of the compartments.

The control unit can check whether an actual position of the vessel on the rotor corresponds to the target position. The control unit can check whether the actual position of the vessel on the rotor corresponds to the target position based on a quality of a signal transmitted from the integrated circuit of the vessel to the control unit.

A plurality of consumables can be provided. The control unit can identify and/or locate one of the consumables by issuing a command and receiving a response signal from the one consumable.

A system comprising a laboratory instrument for processing a reagent or biological sample, a consumable and a RFID tag associated with the consumable is disclosed. The RFID tag can comprise a memory. The memory can comprise a user memory configured to store user data and a system memory configured to store system data of an integrated circuit. The laboratory instrument can be configured to the above methods. Temporary data can be written in the system memory. The system memory can comprise special function bytes. The special function bytes can be configured to temporary store the temporary data.

The consumable can be at least one element selected from the group comprising: reagent vessel, biological sample vessel, pipetting tip, and cuvette.

The process can comprise process steps. The temporary data can be associated with the process steps. The laboratory instrument can be configured to write the temporary data into the system memory each time the consumable enters one of the process steps and can be cleared when the consumable terminates one of the process steps. Otherwise, with faulty termination of the process, it can be used to restore the original correct configuration/loading. The temporary data can comprise information on the consumable.

The laboratory instrument can comprise a control unit. The control unit can be configured to write the temporary data into the system memory. The control unit can be configured to read the temporary data written into the system memory. The control unit can be configured to issue a command for transmitting the temporary data written into the system memory. The control unit can comprise an antenna configured to read the temporary data.

The information can include at least one element selected from the group comprising: target position of the consumable, actual position of the consumable, state of the consumable, type of the consumable and content of the consumable.

The consumable can be a vessel configured to store a reagent or biological sample. The laboratory instrument can comprise a rotor comprising a plurality of compartments configured to receive the vessel. The temporary data can comprise information on a target position of the vessel on the rotor. The target position can be associated with one of the compartments.

The control unit can be configured to check whether an actual position of the vessel on the rotor corresponds to the target position. The control unit can be configured to check whether the actual position of the vessel on the rotor corresponds to the target position based on a quality of a signal transmitted from the integrated circuit of the vessel to the control unit.

The system can further comprise a plurality of consumables. The control unit can be configured to identify one of the consumables by issuing a command and receiving a response signal from the one consumable.

Referring initially to FIG. 1, FIG. 1 shows a perspective view of a system 100 comprising a laboratory instrument 102 for processing a reagent or a biological sample, at least one consumable 104 and a RFID tag 106 associated with the consumable 104. The consumable 104 may be at least one element selected from the group comprising: reagent vessel, biological sample vessel, pipetting tip, and cuvette. In one embodiment, the consumable can be a reagent vessel 108 and the RFID tag may adhere to a side of the reagent vessel 108. The laboratory instrument 102 can comprise a rotor 110. The rotor 110 can comprise a plurality of compartments 112 configured to receive the reagent vessel 108 or a plurality of reagent vessels 108.

Figure 2:
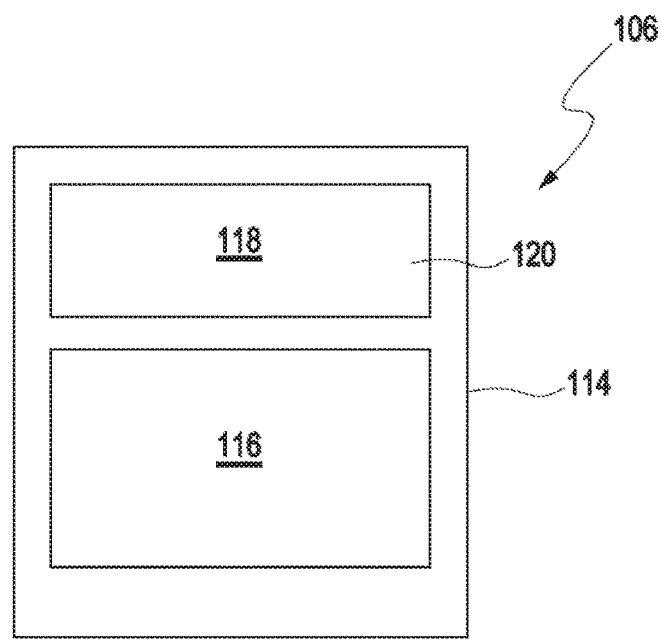
FIG. 2 illustrates an enlarged view of an RIFD tag of the system according to an embodiment of the present disclosure.

FIG. 2 shows an enlarged view of the RFID tag 106 as used in connection with the disclosed method/system. The RFID tag 106 can comprise a memory 114. The memory 114 can be separated into at least two parts as will be explained in further detail below. In one embodiment, the memory 114 can comprise a user memory 116 configured to store user data and a system memory 118 configured to store system data. For example, the memory 114 may be organized based on the ISO standards ISO/IEC 15693. Direct read/write access to the user memory 116 can be possible depending on the related write protection conditions. Within the system memory 118, all required information can be stored such as unique identifier, write protection, access control information, passwords, application family identifier and electronic article surveillance. The system memory 118 cannot be directly accessed. In one embodiment, the unique identifier cannot be altered and can guarantee the uniqueness of each RFID tag. As mentioned, the system memory 118 can be password protected which can enable the addressed RFID tag 106 to be set in a mode where the electronic article surveillance status and the application family identifier value can only be changed if the correct password is transmitted to the RFID tag within predetermined commands.

Further, the system memory 118 can comprise special function bytes 120. The laboratory instrument 102 can be configured to write temporary data into the system memory 118. The temporary data can be associated with the process to be carried out by the laboratory instrument 102. According to the disclosed method/system, the special function bytes 120 can be configured to temporary store the temporary data. The temporary data can be associated with the process steps. The laboratory instrument 102 can write the temporary data into the system memory 118 each time the consumable and thus one of the process steps can be cleared when the consumable terminates one of the process steps.

As shown in FIG. 1, for this purpose, the laboratory instrument 102 can further comprise a control unit 122. The control unit 122 can be configured to write the temporary data into the system memory 118. The control unit 122 can also be configured to read the temporary data written into the system memory 118. For this purpose, the control unit 122 can comprise an antenna 124 such as a RFID reader antenna configured to read the temporary data. Further, the control unit 122 can be configured to issue a command for transmitting the temporary data written into the system memory 118. Thus, when the control unit 122 issues a command, the temporary data can be transmitted from the RFID tag 106 of the consumable 104 and received by the antenna 124.

Figure 3:
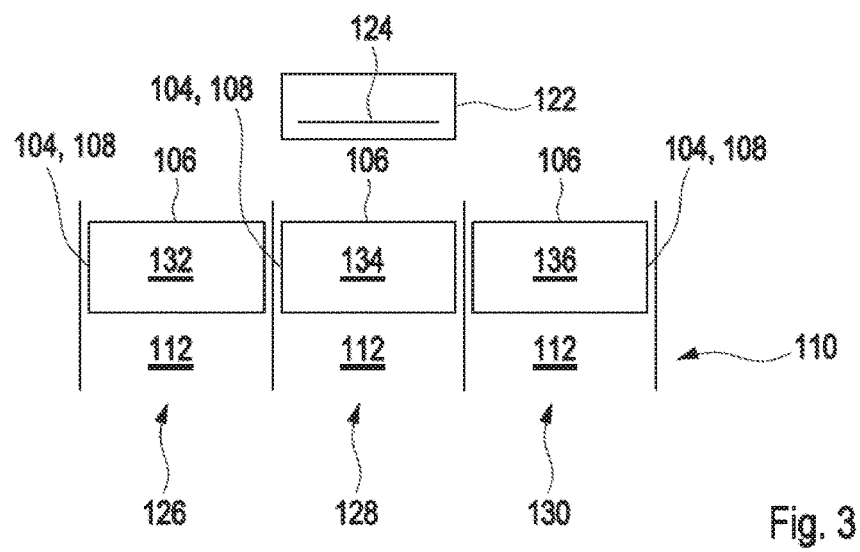
FIG. 3 illustrates a schematic illustration of the operation of the system according to an embodiment of the present disclosure.
Figure 4:
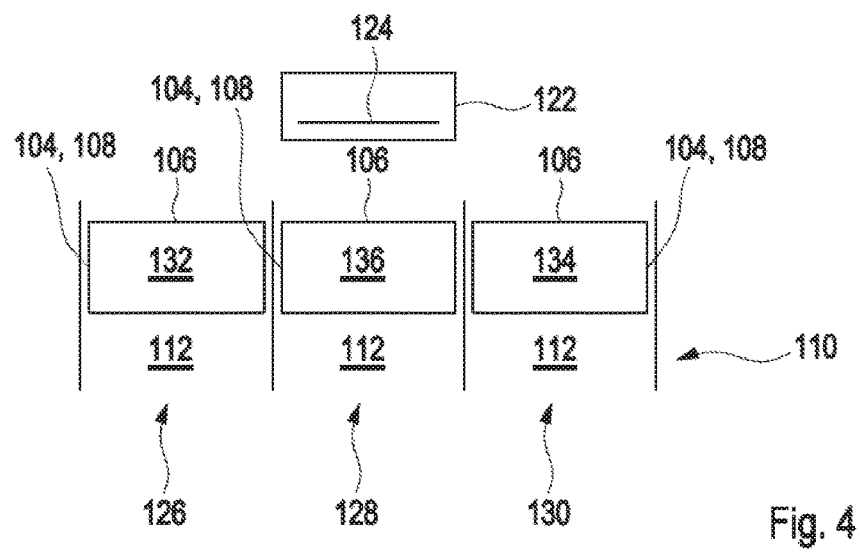
FIG. 4 illustrates another schematic illustration of the operation of the system according to an embodiment of the present disclosure.
Figure 5:
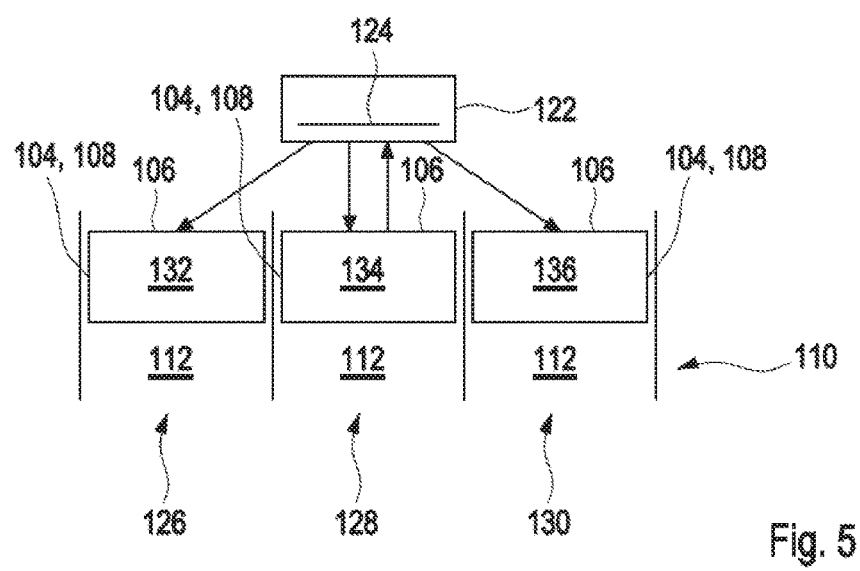
FIG. 5 illustrates yet another schematic illustration of the operation of the system according to an embodiment of the present disclosure.

FIGS. 3-5 show possible operations of the system 100. As mentioned above, the laboratory instrument 102 can comprise the rotor 110. The rotor 110 can comprise the plurality of compartments 112 for receiving a plurality of reagent vessels 108. The temporary data may comprise information on a target position of the reagent vessel 108 on the rotor 110. In other words, the temporary data can include information on which location a reagent vessel 108 is to be disposed. Thus, the target position can be associated with one of the compartments 112. The control unit 122 can be configured to check whether an actual position of the reagent vessel 108 on the rotor 110 corresponds to the target position. For example, the control unit 122 can be configured to check whether the actual position of the vessel 108 and rotor 112 corresponds to the target position based on a quality of a signal transmitted from the RFID tag 106 of the reagent vessel 108 to the control unit 122 as will be explained in more detail below, a distance from the second system memory FIG. 3 shows a schematic illustration of the operation of the system. For explanatory reasons, the rotor 110 and the compartments 112 are shown in a simplified manner in FIG. 3. The compartments 112 can represent different rotor positions. In FIG. 3, a first rotor position 126 is shown on the left, a second rotor position 128 is shown in the middle and a third rotor position 130 is shown on the right. Needless to say, the plurality of compartments 112 may represent more than three rotor positions such as, for example, 4, 5, 10, 20, 30 or even more. Further shown in FIG. 3 are three reagent vessels 108, each one of which can be stored in one of the compartments 112. The reagent vessels 108 are illustrated in a simplified manner such that only the system memories of the reagent vessels 108 are illustrated. A first system memory 132 is shown at the first rotor position 126, a second system memory 134 is shown at the second rotor position 128 and a third system memory 136 is shown at the third rotor position 130. In the first system memory 132, temporary data can be stored comprising information that the target position of this reagent vessel 108 is the first rotor position 126. In the second system memory 134, temporary data can be stored comprising information that the target position of this reagent vessel 108 is the second rotor position 128. In the third system memory 136, temporary data can be stored comprising information that the target position of this reagent vessel 108 is the third rotor position 130. A distance from the second rotor position 128 to the antenna 124 of the control unit 122 can be closer than a distance from the first rotor position 126 or the third rotor position 130 to the antenna 124. If the control unit 122 issues a communication command for checking whether the reagent vessels 108 are arranged on their correct position, the control unit 122 may check the response signal strength. In the example shown in FIG. 3, the control unit 122 can check whether the reagent vessel 108 at the second rotor position 128 is at its correct position. Accordingly, the rotor 110 can be rotated such that the second rotor position 128 faces the antenna 124. The control unit 122 can issue a communication command to the reagent vessel 108 at the second rotor position 128. As in the second system memory 134, temporary data can be stored comprising information that the target position of this reagent vessel 108 is the second rotor position 128 and the second system memory 134 is disposed at the second rotor position 128, the response signal transmitted to the antenna 124 can comprise the full strength due to the shortest possible distance to the antenna 124. Thereby, the control unit 122 can determine a match of the special function bytes values of the second system memory 134 and the second rotor position 128. In other words, the control unit 122 can determine that the actual position of the reagent vessel 108 at the second rotor position 128 corresponds to the target position thereof.

FIG. 4 shows a schematic illustration of the operation of the system. In one embodiment, FIG. 4 shows the case where the reagent vessels 108 have been changed such that the second system memory 134 is disposed at the third rotor position 130 while the third system memory 136 is disposed at the second rotor position 128. In the example shown in FIG. 4, the control unit 122 can check whether the reagent vessel 108 at the second rotor position 128 is at its correct position. Accordingly, the rotor 110 can be rotated such that the second rotor position 128 can face the antenna 124. The control unit 122 can issue a communication command to the reagent vessel 108 at the second rotor position 128. As in the second system memory 134, temporary data can be stored comprising information that the target position of this reagent vessel 108 is the second rotor position 128 and the second system memory 134 is disposed at the third rotor position 130, the response signal transmitted to the antenna 124 can comprise less strength than in the example shown in FIG. 3 due to the longer distance to the antenna 124. Thereby, the control unit 122 can determine a mismatch of the special function bytes values of the second system memory 134 and the second rotor position 128. In other words, the control unit 122 can determine that the actual position of the reagent vessel 108 at the second rotor position 128 does not correspond to the target position thereof.

FIG. 5 shows a schematic illustration of the operation of the system. In one embodiment, the control unit 122 may be configured to identify a predetermined reagent vessel 108 by issuing a specific command. In the shown example representing a multiple tagged item scenario, i.e., one reader antenna 124 with multiple RFID tags in the electro-magnetic field of the reader, the rotor position id can be correlated to one of the RFID tags in the field without the use of any receive signal evaluation algorithms. Furthermore by sending a command with the rotor position id as parameter only that specific RFID tag can respond saving communication time. For example, the control unit 122 can issue the command "I want to communicate with RFID tag 106 on the second rotor position 128." Then, the control unit 122 can communicate with the second system memory 134 shown in the middle provided the actual position thereof corresponds to the target position thereof. In this case, the antenna 124 can receive a response signal exclusively from the RFID tag on the second rotor position 128.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method for storing temporary data in a memory of a RFID tag associated with a consumable of a laboratory instrument for processing a reagent or biological sample, the method comprising:
   providing the RFID tag associated with the consumable, wherein the RFID tag comprises a memory, wherein the memory comprises a user memory configured to store user data and a system memory configured to store system data;
   writing the temporary data by the laboratory instrument into the system memory, wherein the temporary data are associated with a process to be carried out by the laboratory instrument, wherein the temporary data comprise information on the consumable, and wherein the information includes at least state of the consumable or type of the consumable; and
   clearing the temporary data from the system memory during the process of the laboratory instrument.

2. The method according to claim 1, wherein the system memory comprises special function bytes, wherein the special function bytes are used to store the temporary data.

3. The method according to claim 1, wherein the process comprises process steps, wherein the temporary data are associated with the process steps, wherein the temporary data are written into the system memory each time the consumable enters one of the process steps and are cleared when the consumable terminates one of the process steps.

4. The method according to claim 1, wherein the information includes at least one element selected from the group comprising: target position of the consumable, actual position of the consumable, and content of the consumable.

5. The method according to claim 1, further comprise, wherein a control unit reads the temporary data written into the system memory.

6. The method according to claim 5, wherein the consumable is a vessel configured to store a reagent or biological sample, wherein the laboratory instrument comprises a rotor comprising a plurality of compartments configured to receive the vessel, wherein the temporary data comprise information on a target and/or actual position of the vessel on the rotor, wherein the target position is associated with one of the compartments.

7. The method according to claim 6, wherein the control unit checks whether an actual position of the vessel on the rotor corresponds to the target position.

8. The method according to claim 5, wherein a plurality of consumables is provided, wherein the control unit identifies and/or locates one of the consumables by issuing a command and receiving a response signal from the one consumable.

9. A system, the system comprising:
   a laboratory instrument for processing a reagent or biological sample;
   a consumable; and
   a RFID tag associated with the consumable, wherein the RFID tag comprises a memory, wherein the memory comprises a user memory configured to store user data and a system memory configured to store system data of the integrated circuit, wherein the laboratory instrument is configured to carry out a method, the method comprising:

providing the RFID tag associated with the consumable, wherein the RFID tag comprises a memory, wherein the memory comprises a user memory configured to store user data and a system memory configured to store system data;

writing the temporary data by the laboratory instrument into the system memory, wherein the temporary data are associated with a process to be carried out by the laboratory instrument, wherein the temporary data comprise information on the consumable, and wherein the information includes at least state of the consumable or type of the consumable; and clearing the temporary data from the system memory during the process of the laboratory instrument.

10. The system according to claim 9, wherein the consumable is at least one element selected from the group comprising: reagent vessel, biological sample vessel, pipetting tip, and cuvette.

11. The system according to claim 9, wherein temporary data are written in the system memory.

12. The system according to claim 11, wherein the system memory comprises special function bytes, wherein the special function bytes are configured to temporary store the temporary data.

13. The system according to claim 11, wherein the process comprises process steps, wherein the temporary data are associated with the process steps.

14. The system according to claim 13, wherein the laboratory instrument is configured to write the temporary data into the system memory each time the consumable enters one of the process steps and are cleared when the consumable terminates one of the process steps.

15. The system according to claim 11, wherein the laboratory instrument comprises a control unit.

16. The system according to claim 11, wherein the control unit is configured to write the temporary data into the system memory and/or to read the temporary data written into the system memory.

17. The system according to claim 11, wherein the information includes at least one element selected from the group consisting of: target position of the consumable, actual position of the consumable, and content of the consumable.

18. The system according to claim 11, wherein the consumable is a vessel configured to store a reagent or biological sample.

19. The system according to claim 18, wherein the laboratory instrument comprises a rotor comprising a plurality of compartments configured to receive the vessel.

20. The system according to claim 19, wherein the temporary data comprise information on a target position of the vessel on the rotor, wherein the target position is associated with one of the compartments.

* * * * *